(12) United States Patent
Kumar et al.

(10) Patent No.: US 10,875,833 B2
(45) Date of Patent: Dec. 29, 2020

(54) ALIGNMENT COMPOUNDS

(71) Applicant: Transitions Optical, Inc., Pinellas Park, FL (US)

(72) Inventors: Anil Kumar, Murrysville, PA (US); Ryan Stayshich, Pittsburgh, PA (US); Meng He, Palm Harbor, FL (US); Gobinda Saha, Pittsburgh, PA (US)

(73) Assignee: Transitions Optical, Inc., Pinellas Park, FL (US)

( * ) Notice: Subject to any disclaimer, the term of this patent is extended or adjusted under 35 U.S.C. 154(b) by 0 days.

(21) Appl. No.: 15/573,212

(22) PCT Filed: Jun. 12, 2015

(86) PCT No.: PCT/US2015/035546
§ 371 (c)(1),
(2) Date: Nov. 10, 2017

(87) PCT Pub. No.: WO2016/200401
PCT Pub. Date: Dec. 15, 2016

(65) Prior Publication Data
US 2018/0086725 A1     Mar. 29, 2018

(51) Int. Cl.

| | | |
|---|---|---|
| C07D 263/57 | (2006.01) | |
| C07D 277/66 | (2006.01) | |
| C07D 307/80 | (2006.01) | |
| C07D 333/56 | (2006.01) | |
| C07D 498/04 | (2006.01) | |
| C08F 220/38 | (2006.01) | |
| C08F 220/30 | (2006.01) | |
| C08F 220/36 | (2006.01) | |
| C09K 19/56 | (2006.01) | |

(52) U.S. Cl.
CPC ......... *C07D 263/57* (2013.01); *C07D 277/66* (2013.01); *C07D 307/80* (2013.01); *C07D 333/56* (2013.01); *C07D 498/04* (2013.01); *C08F 220/30* (2013.01); *C08F 220/36* (2013.01); *C08F 220/38* (2013.01); *C09K 19/56* (2013.01); *C08F 220/303* (2020.02); *C08F 220/382* (2020.02); *C08F 220/387* (2020.02)

(58) Field of Classification Search
CPC .. C07D 263/57; C07D 498/04; C07D 333/56; C07D 307/80; C07D 277/66; C08F 2220/387; C08F 2220/303; C08F 2220/382; C08F 220/38; C08F 220/36; C08F 220/30; C08F 220/387; C08F 220/382; C08F 220/303; C09K 19/56
See application file for complete search history.

(56) References Cited

U.S. PATENT DOCUMENTS

| | | | |
|---|---|---|---|
| 4,978,476 A * | 12/1990 | Allen | G02F 1/3617 252/299.01 |
| 5,645,767 A | 7/1997 | Van Gemert | |
| 6,849,203 B2 | 2/2005 | Farrand et al. | |
| 6,939,479 B2 | 9/2005 | Farrand et al. | |
| 7,256,921 B2 | 8/2007 | Kumar et al. | |
| 8,349,210 B2 | 1/2013 | Xu et al. | |
| 8,431,039 B2 | 4/2013 | Dai et al. | |
| 8,613,868 B2 | 12/2013 | Dai et al. | |
| 8,623,238 B2 | 1/2014 | Xu et al. | |
| 8,828,365 B2 * | 9/2014 | Hotz | A61K 8/8111 424/59 |
| 2003/0099785 A1 | 5/2003 | O'Neill et al. | |
| 2011/0135850 A1 | 6/2011 | Saha et al. | |
| 2012/0003401 A1 | 1/2012 | Xu et al. | |

FOREIGN PATENT DOCUMENTS

| | | | | |
|---|---|---|---|---|
| CN | 103050629 A | * | 4/2013 | |
| WO | WO-2007091313 A1 | * | 8/2007 | ........... C07D 263/56 |
| WO | WO-2016025424 A1 | * | 2/2016 | ........... C07D 417/06 |

OTHER PUBLICATIONS

Kim, S., "Synthesis of liquid crystalline monomers and side-chain polymers containing 2-phenylbenzoxazole in mesogenic unit." Bulletin of the Korean Chemical Society 20.4 (1999): 473-477.*
Namil, A., "Synthesis of 4-N, N-dialkylaminoethyl-2-indolones as potential dopamine agonists." European journal of medicinal chemistry 30.12 (1995): 973-981.*
CN 103050629 A , Apr. 2013; WIPO English machine translation; accessed online Dec. 26, 2018; p. 1-65.*
WO-2007091313-A1 (2007) WIPO English Machine Translation p. 1-36.*
CAS CaPlus Database entries 886063-17-8 (2006) and 654078-45-2 (2004) p. 1.*
Oxford English Dictionary (2019) mesogen & mesogenic n. (accessed online at https://www.oed.com/) p. 1-3.*
Roussilhe et al., "Photodimerization of 2-Phenylbenzoxazole and its Acid-catalysed Reversion as a New System for Light Energy Conversion", Journal of the Chemical Society, Chemical Communications, 1982, pp. 380-381.
Roussilhe et al., "Photochemical of 2-Phenylbenzoxazole, Synthesis of 1,3-Diazetidine via the Intermolecular [2π+2π] Cycloaddition of Two Carbon-Nitrogen Double Bonds", Journal of Organic Chemistry, 1983, vol. 48, pp. 3736-3741.

\* cited by examiner

*Primary Examiner* — John M Mauro
(74) *Attorney, Agent, or Firm* — The Webb Law Firm

(57) ABSTRACT

The present invention relates to compounds represented by the following Formula (I). With reference to Formula (I), at least one of $E^1$ and $E^2$ independently is, or is independently substituted with, at least one reactive group, such as a (meth)acryloyl group. The compounds of the present invention can be used alone and/or in combination with polymers prepared from such compounds, such as to form or as one or more components of an alignment layer.

(I)

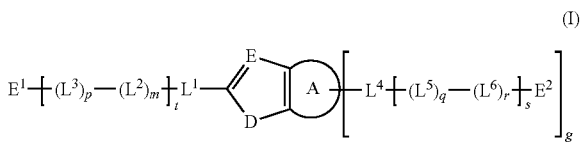

9 Claims, No Drawings

ALIGNMENT COMPOUNDS

CROSS-REFERENCE TO RELATED APPLICATION

This application is the United States national phase of International Application No. PCT/US2015/035546 filed Jun. 12, 2015, which is incorporated herein by reference in its entirety.

FIELD

The present invention relates to compounds that have alignment properties, such as photoalignment properties, which can be used to prepare alignment materials, such as polymers.

BACKGROUND

Liquid crystal materials are used in various applications. Typically, the liquid crystal materials are formed as a layer over the surface of a substrate, such as an ophthalmic lens. To obtain desired properties and performance, the liquid crystal materials of the liquid crystal containing layer are typically orientated or aligned along a common direction. Alignment of the liquid crystal materials can be achieved by contact of the liquid crystal containing layer with an underlying alignment layer. Orientation of the alignment layer can be achieved by physical methods, such as rubbing, and/or remote methods, such as exposure to electromagnetic radiation.

Alignment of the alignment layer and correspondingly the liquid crystal materials of the liquid crystal containing layer by remote methods, such as by exposure to electromagnetic radiation, can be desirable compared to physical methods. Physical alignment methods can have associated therewith disadvantages, such as dirt pickup by and/or corruption, such as tearing, of the alignment layer. Remote alignment methods are generally not subject to such disadvantages, and can be advantageously used to define distinct areas across the alignment layer having different alignment directions.

It would be desirable to develop new compounds that themselves have alignment properties, and/or which can be used to prepare materials, such as polymers having alignment properties. It would be further desirable that such newly developed compounds, and/or materials prepared therefrom, can be remotely aligned, such as by exposure to electromagnetic radiation.

SUMMARY

In accordance with the present invention, there is provided a compound represented by the following Formula (I):

Formula (I)

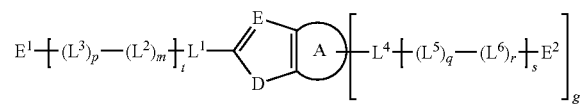

With reference to Formula (I): Ring-A is selected from the group consisting of aryl and heteroaryl; E is N or C—$R^1$; and D is selected from the group consisting of O, S, and N—$R^2$.

With further reference to Formula (I), $R^1$ of E and $R^2$ of D are each independently selected from the group consisting of hydrogen, hydrocarbyl, substituted hydrocarbyl, interrupted hydrocarbyl, and substituted interrupted hydrocarbyl, wherein each interrupted hydrocarbyl and each substituted interrupted hydrocarbyl are each independently interrupted with at least one interrupting group selected from the group consisting of —O—, —S—, —C(O)—, —C(O)O—, —S(O)—, —SO$_2$—, —N═N—, —N($R_{11}$')— where $R_{11}$' is selected from the group consisting of hydrogen, hydrocarbyl or substituted hydrocarbyl, —Si(O$R_8$')$_w$($R_8$')$_e$—, where w and e are each independently 0 to 2, provided that the sum of w and e is 2, and each $R_8$' is independently selected from the group consisting of hydrogen, hydrocarbyl and substituted hydrocarbyl, and combinations of two or more interrupting groups thereof.

With additional reference to Formula (I), $L^1$ and $L^4$ are each independently selected from at least one of: a single bond; —O—; —S—; —C(O)—; —S(O)—; —SO$_2$—; —N═N—; —N($R_{11}$')— where $R_{11}$' is selected from the group consisting of hydrogen, hydrocarbyl or substituted hydrocarbyl; —Si(O$R_8$')$_w$($R_8$')$_e$—, where w and e are each independently 0 to 2, provided that the sum of w and e is 2, and each $R_8$' is independently selected from the group consisting of hydrogen, hydrocarbyl and substituted hydrocarbyl; hydrocarbyl; substituted hydrocarbyl; interrupted hydrocarbyl; and substituted interrupted hydrocarbyl, wherein each interrupted hydrocarbyl and each substituted interrupted hydrocarbyl are each independently interrupted with at least one interrupting group selected from the group consisting of —O—, —S—, —C(O)—, —C(O)O—, —S(O)—, —SO$_2$—, —N═N—, —N($R_{11}$')— where $R_{11}$' is selected from the group consisting of hydrogen, hydrocarbyl or substituted hydrocarbyl, —Si(O$R_8$')$_w$($R_8$')$_e$—, where w and e are each independently 0 to 2, provided that the sum of w and e is 2, and each $R_8$' is independently selected from the group consisting of hydrogen, hydrocarbyl and substituted hydrocarbyl, and combinations of two or more interrupting groups thereof.

With further reference to Formula (I): t is 0 to 4, or 1 to 4; s is, independently for each g, from 1 to 4; g is 0 to 6, provided that the sum of t and g is at least 1; m is, independently for each t, from 0 to 4; and q is, independently for each s, from 0 to 4.

With additional reference to Formula (I), $L^2$ independently for each m, and $L^5$ independently for each q, are in each case independently selected from the group consisting of divalent linear or branched $C_1$-$C_{25}$ alkyl, divalent interrupted linear or branched $C_1$-$C_{25}$ alkyl, divalent linear or branched $C_1$-$C_{25}$ perhaloalkyl, divalent interrupted linear or branched $C_1$-$C_{25}$ perhaloalkyl, divalent linear or branched $C_2$-$C_{25}$ alkenyl, and divalent interrupted linear or branched $C_2$-$C_{25}$ alkenyl, wherein each divalent interrupted linear or branched $C_1$-$C_{25}$ alkyl, each divalent interrupted linear or branched $C_1$-$C_{25}$ perhaloalkyl, and each divalent interrupted linear or branched $C_2$-$C_{25}$ alkenyl are each independently interrupted with at least one interrupting group selected from the group consisting of —O—, —S—, —C(O)—, —C(O)O—, —OC(O)O—, —S(O)—, —SO$_2$—, —N($R^9$)—, and —Si($R^9$)($R^{10}$)— wherein $R^9$ and $R^{10}$ are each independently selected from the group consisting of hydrogen, hydrocarbyl and substituted hydrocarbyl, and combinations of two or more interrupting groups thereof.

With further reference to Formula (I): p is, independently for each t, from 0 to 4, provided the sum of m and p is at least 1 for each t that is greater than zero; and r is, independently for each s, from 0 to 4, provided the sum of q and r is at least 1 for each s.

With additional reference to Formula (I), $L^3$ independently for each p, and $L^6$ independently for each r, are in each case independently represented by the following Formula (II-1),

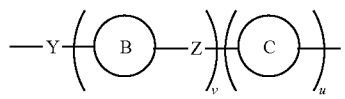

Formula (II-1)

With reference to Formula (II-1), Y is, independently for each p and independently for each r, a divalent linking group selected from the group consisting of a single bond, —O—, —S—, —C(O)—, —C(O)O—, —OC(O)O—, —S(O)—, —SO$_2$—, —N(R$^9$)—, —N(R$^9$)—C(O)—O—, —C(O)—N (R$^9$)—, and —Si(R$^9$)(R$^{10}$)— wherein R$^9$ and R$^{10}$ are each independently selected from the group consisting of hydrogen, hydrocarbyl and substituted hydrocarbyl.

With further reference to Formula (II-1), v and u are each independently, for each p and each r, 0 to 5, provided that the sum of v and u is at least 1 for each p that is greater than zero and each r that is greater than zero.

With additional reference to Formula (II-1), Z is, independently for each v, a divalent linking group selected from the group consisting of a single bond, —O—, —S—, —C(O)—, —C(O)O—, —OC(O)O—, —S(O)—, —SO$_2$—, —N(R$^9$)—, —N(R$^9$)—C(O)—O—, —C(O)—N(R$^9$)—, and —Si(R$^9$)(R$^{10}$)— wherein R$^9$ and R$^{10}$ are each independently selected from the group consisting of hydrogen, hydrocarbyl and substituted hydrocarbyl.

With further reference to Formula (II-1), the divalent rings,

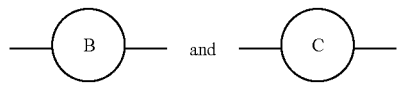

are each independently selected, for each v and each u, from the group consisting of divalent aryl, substituted divalent aryl, divalent heteroaryl, substituted divalent heteroaryl, divalent cycloalkyl, substituted divalent cycloalkyl, divalent heterocycloalkyl, and substituted divalent heterocycloalkyl.

With reference again to Formula (I), $E^1$ and $E^2$ are each independently selected from the group consisting of hydrogen, hydrocarbyl, interrupted hydrocarbyl, substituted hydrocarbyl, and substituted interrupted hydrocarbyl, wherein each interrupted hydrocarbyl and each substituted interrupted hydrocarbyl are each independently interrupted with at least one interrupting group selected from the group consisting of —O—, —S—, —C(O)—, —C(O)O—, —OC(O)O—, —S(O)—, —SO$_2$—, —N(R$^9$)—, and —Si(R$^9$)(R$^{10}$)— wherein R$^9$ and R$^{10}$ are each independently selected from the group consisting of hydrogen, hydrocarbyl and substituted hydrocarbyl, and combinations of two or more interrupting groups thereof.

With regard to $E^1$ and $E^2$ of Formula (I), there is the proviso that at least one of $E^1$ and $E^2$ independently is, or is independently substituted with, at least one reactive group selected from the group consisting of (linear or branched $C_1$-$C_8$ alkyl)acryloyl, unsubstituted styrene, substituted styrene, oxirane, thiirane, carboxylic acid, carboxylic acid ester, unsubstituted cyclic carboxylic acid ester, substituted cyclic carboxylic acid ester, cyclic carboxylic acid anhydride, hydroxyl, thiol, amine, isocyanate, aldehyde, and combinations thereof.

With further reference to Formula (I), there are the following further provisos: a direct $L^1$-$L^2$ link between $L^1$ and $L^2$ is free of two heteroatoms linked together; a direct $L^1$-$L^3$ link between $L^1$ and $L^3$ is free of two heteroatoms linked together; and each direct $L^2$-$L^3$ link between each directly linked $L^2$ and $L^3$ is free of two heteroatoms linked together.

With additional reference to Formula (I), there are the following additional provisos: a direct $L^4$-$L^5$ link between $L^4$ and $L^5$ is free of two heteroatoms linked together; a direct $L^4$-$L^6$ link between $L^4$ and $L^6$ is free of two heteroatoms linked together; and each direct $L^5$-$L^6$ link between each directly linked $L^5$ and $L^6$ is free of two heteroatoms linked together.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

DETAILED DESCRIPTION

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

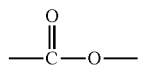

or equivalently —C(O)O—, is inclusive of the right-to-left representation thereof,

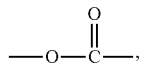

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, molecular weight values of polymers, such as weight average molecular weights (Mw) and number average molecular weights (Mn), are determined by gel permeation chromatography using appropriate standards, such as polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

The compounds of the present invention are also referred to herein as alignment compounds and/or alignment monomers.

The compounds of the present invention, as described herein, including, but not limited to, compounds represented by Formula (I), in each case can optionally further include one or more coproducts, resulting from the synthesis of such compounds.

As used herein, the term "actinic radiation" means electromagnetic radiation that is capable of causing a response in a material, such as, but not limited to, transforming compounds according to the present invention, and/or materials prepared therefrom, from a non-aligned arrangement to an aligned arrangement.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein the term "optical" means pertaining to or associated with light and/or vision. For example, according to various non-limiting embodiments disclosed herein, the optical article or element or device can be chosen from ophthalmic articles, elements and devices, display articles, elements and devices, windows, mirrors, and active and passive liquid crystal cell articles, elements and devices.

As used herein the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein the term "display" means the visible or machine-readable representation of information in words, numbers, symbols, designs or drawings. Non-limiting examples of display elements include screens, monitors, and security elements, such as security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein the term "liquid crystal cell" refers to a structure containing a liquid crystal material that is capable of being ordered. A non-limiting example of a liquid crystal cell element is a liquid crystal display.

As used herein, the term "mesogen" and similar terms, such as "mesogen group," "mesogenic," and "mesogenic group," means the fundamental unit (or segment or group) of a liquid crystal material that induces, and/or is induced into, structural order amongst and between liquid crystals, such as (but not limited to) liquid crystal materials that are together present in a liquid crystal composition.

As used herein, spatial or directional terms, such as "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," "residing over," or "positioned over," mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

All documents, such as but not limited to issued patents and patent applications, referred to herein, and unless otherwise indicated, are to be considered to be "incorporated by reference" in their entirety.

As used herein, the term "a bond" such as used with, but not limited to, $L^1$, $L^4$, Y, and Z, means a single bond.

As used herein, recitations of "linear or branched" groups, such as linear or branched alkyl, are herein understood to include: a methylene group or a methyl group; groups that are linear, such as linear $C_2$-$C_{20}$ alkyl groups; and groups that are appropriately branched, such as branched $C_3$-$C_{20}$ alkyl groups.

As used herein, recitations of "optionally substituted" group, means a group, including but not limited to, alkyl group, cycloalkyl group, heterocycloalkyl group, aryl group, and/or heteroaryl group, in which at least one hydrogen thereof has been optionally replaced or substituted with a group that is other than hydrogen, such as, but not limited to, halo groups (e.g., F, Cl, I, and Br), hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (including, but not limited to: alkyl; alkenyl; alkynyl; cycloalkyl, including poly-fused-ring cycloalkyl and polycyclocalkyl; heterocycloalkyl; aryl, including hydroxyl substituted aryl, such as phenol, and including poly-fused-ring aryl; heteroaryl, including poly-fused-ring heteroaryl; and aralkyl groups), and amine groups, such as —N($R_{11}$')($R_{12}$') where $R_{11}$' and $R_{12}$' are each independently selected, with some embodiments, from hydrogen, linear or branched $C_1$-$C_{20}$ alkyl, $C_3$-$C_{12}$ cycloalkyl, $C_3$-$C_{12}$ heterocycloalkyl, aryl, and heteroaryl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to perhaloalkyl groups, perhaloalkenyl groups, perhaloalkynyl groups, perhaloaryl groups and perhalo-heteroaryl groups) means a group in which all of the available hydrogen groups thereof are substituted with a halo group. For example, perhalomethyl is —$CX_3$; perhalo-phenyl is —$C_6X_5$, where X represents one or more halo groups, such as, but not limited to F.

The compounds of the present invention include groups and sub-groups that can in each case be independently selected from hydrocarbyl and/or substituted hydrocarbyl. As used herein the term "hydrocarbyl" and similar terms, such as "hydrocarbyl substituent," means: linear or branched $C_1$-$C_{25}$ alkyl (e.g., linear or branched $C_1$-$C_{10}$ alkyl); linear or branched $C_2$-$C_{25}$ alkenyl (e.g., linear or branched $C_2$-$C_{10}$ alkenyl); linear or branched $C_2$-$C_{25}$ alkynyl (e.g., linear or branched $C_2$-$C_{10}$ alkynyl); $C_3$-$C_{12}$ cycloalkyl (e.g., $C_3$-$C_{10}$ cycloalkyl); $C_3$-$C_{12}$ heterocycloalkyl (having at least one hetero atom in the cyclic ring); $C_5$-$C_{18}$ aryl (including polycyclic aryl groups) (e.g., $C_5$-$C_{10}$ aryl); $C_5$-$C_{18}$ heteroaryl (having at least one hetero atom in the aromatic ring); and $C_6$-$C_{24}$ aralkyl (e.g., $C_6$-$C_{10}$ aralkyl).

Representative alkyl groups include but are not limited to methyl, ethyl, propyl, isopropyl, butyl, isobutyl, sec-butyl, tert-butyl, pentyl, neopentyl, hexyl, heptyl, octyl, nonyl and decyl. Representative alkenyl groups include but are not limited to vinyl, allyl and propenyl. Representative alkynyl groups include but are not limited to ethynyl, 1-propynyl, 2-propynyl, 1-butynyl, and 2-butynyl. Representative cycloalkyl groups include but are not limited to cyclopropyl, cyclobutyl, cyclopentyl, cyclohexyl, and cyclooctyl substituents. Representative heterocycloalkyl groups include but are not limited to imidazolyl, tetrahydrofuranyl, tetrahydropyranyl and piperidinyl. Representative aryl groups include but are not limited to phenyl, naphthyl, anthracynyl and triptycenyl. Representative heteroaryl groups include but are not limited to furanyl, pyranyl, pyridinyl, isoquinoline, and pyrimidinyl. Representative aralkyl groups include but are not limited to benzyl, and phenethyl.

The term "substituted hydrocarbyl" as used herein means a hydrocarbyl group in which at least one hydrogen thereof has been substituted with a group that is other than hydrogen, such as, but not limited to, halo groups, hydroxyl groups, ether groups, thiol groups, thio ether groups, carboxylic acid groups, carboxylic acid ester groups, phosphoric acid groups, phosphoric acid ester groups, sulfonic acid groups, sulfonic acid ester groups, nitro groups, cyano groups, hydrocarbyl groups (e.g., alkyl, alkenyl, alkynyl, cycloalkyl, heterocycloalkyl, aryl, heteroaryl, and aralkyl groups), and amine groups, such as —N($R_{11}$')($R_{12}$') where $R_{11}$' and $R_{12}$' are each independently selected from hydrogen, hydrocarbyl and substituted hydrocarbyl.

The term "substituted hydrocarbyl" is inclusive of halohydrocarbyl (or halo substituted hydrocarbyl) substituents. The term "halohydrocarbyl" as used herein, and similar terms, such as halo substituted hydrocarbyl, means that at least one hydrogen atom of the hydrocarbyl (e.g., of the alkyl, alkenyl, alkynyl, cycloalkyl, heterocycloalkyl, aryl, heteroaryl, and aralkyl groups) is replaced with a halogen atom selected from chlorine, bromine, fluorine and iodine. The degree of halogenation can range from at least one hydrogen atom but less than all hydrogen atoms being replaced by a halogen atom (e.g., a fluoromethyl group), to full halogenation (perhalogenation) in which all replaceable hydrogen atoms on the hydrocarbyl group have each been replaced by a halogen atom (e.g., trifluoromethyl or perfluoromethyl). Correspondingly, the term "perhalohydrocarbyl group" as used herein means a hydrocarbyl group in which all replaceable hydrogens have been replaced with a halogen. Examples of perhalohydrocarbyl groups include, but are not limited to, perhalogenated phenyl groups and perhalogenated alkyl groups.

The hydrocarbyl and substituted hydrocarbyl groups from which the various groups described herein can each be independently selected, in some instances and with some embodiments, can in each case be independently interrupted with at least one interrupting group, and when so interrupted are referred to herein as interrupted hydrocarbyl and substituted interrupted hydrocarbyl groups. Each interrupted hydrocarbyl and each substituted interrupted hydrocarbyl, are in each case independently interrupted with at least one interrupting group selected from —O—, —S—, —C(O)—, —C(O)O—, —S(O)—, —$SO_2$—, —N=N—, —N($R_{11}$')— where $R_{11}$' in each case is independently selected from hydrogen, hydrocarbyl or substituted hydrocarbyl, —Si($OR_8$')$_w$($R_8$')$_e$—, where w and t are each independently selected from 0 to 2, provided that the sum of w and e is 2, and each $R_8$' is independently selected from hydrogen, hydrocarbyl and substituted hydrocarbyl, and combinations of two or more interrupting groups thereof. As used herein, by interrupted with at least one interrupting group selected from —O—, —S—, —C(O)—, —C(O)O—, —S(O)—, —$SO_2$—, —N=N—, —N($R_{11}$')— and —Si($OR_8$')$_w$($R_8$')$_e$—, means that at least one carbon of, but less than all of the carbons of, the interrupted hydrocarbyl group or substituted interrupted hydrocarbyl group, is in each case independently replaced with one or more of the recited divalent non-carbon linking groups. The interrupted hydrocarbyl and substituted interrupted hydrocarbyl groups can be interrupted with two or more of the above recited linking groups, which can be adjacent to each other or separated by one or more carbons. For purposes of non-limiting illustration, a combination of adjacent —C(O)— and —N(R$_{11}$')— can provide a divalent amide linking or interrupting group, —C(O)—N(R$_{11}$')—. For purposes of further non-limiting illustration, a combination of adjacent —N(R$_{11}$')—, —C(O)— and —O— can provide a divalent carbamate (or urethane) linking or interrupting group, —N(R$_{11}$')—C(O)—O—, where R$_{11}$' is hydrogen.

The term "interrupted with" as used with regard to the various groups described herein, such as but not limited to interrupted hydrocarbyl and substituted interrupted hydrocarbyl groups, also includes interruption at the initial linking position of the group to the compound or core compound structure with at least one interrupting group selected from —O—, —S—, —C(O)—, —C(O)O—, —S(O)—, —SO$_2$—, —N═N—, —N(R$_{11}$')— where R$_{11}$' in each case is independently selected from hydrogen, hydrocarbyl or substituted hydrocarbyl, —Si(OR$_8$')$_w$(R$_8$')$_e$—, where w and e are each independently selected from 0 to 2, provided that the sum of w and t is 2, and each R$_8$' is independently selected from hydrogen, hydrocarbyl and substituted hydrocarbyl, and combinations of two or more interrupting groups thereof. For purposes of nonlimiting illustration, when an R$^1$ (of C—R$^1$ of E) of Formula (I) is interrupted hydrocarbyl, the R$^1$ interrupted hydrocarbyl group can be interrupted with one or more of the above recited divalent interrupting groups, such as but not limited to —O—: (i) along the hydrocarbyl chain thereof; and/or (ii) at the point where R$^1$ is bonded to the C of C—R$^1$.

The term "alkyl" as used herein, in accordance with some embodiments, means linear or branched alkyl, such as but not limited to, linear or branched $C_1$-$C_{25}$ alkyl, or linear or branched $C_1$-$C_{10}$ alkyl, or linear or branched $C_2$-$C_{10}$ alkyl. Examples of alkyl groups from which the various alkyl groups of the present invention can be selected from, include, but are not limited to, those recited previously herein. Alkyl groups of the various compounds of the present invention can, with some embodiments, include one or more unsaturated linkages selected from —CH═CH— groups and/or one or more —C≡C— groups, provided the alkyl group is free of two or more conjugated unsaturated linkages. With some embodiments, the alkyl groups are free of unsaturated linkages, such as —CH═CH— groups and —C≡C— groups.

The term "cycloalkyl" as used herein, in accordance with some embodiments, means groups that are appropriately cyclic, such as but not limited to, $C_3$-$C_{12}$ cycloalkyl (including, but not limited to, cyclic $C_5$-$C_7$ alkyl) groups. Examples of cycloalkyl groups include, but are not limited to, those recited previously herein. The term "cycloalkyl" as used herein in accordance with some embodiments also includes: bridged ring polycycloalkyl groups (or bridged ring polycyclic alkyl groups), such as but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein, in accordance with some embodiments, means groups that are appropriately cyclic, such as but not limited to, $C_3$-$C_{12}$ heterocycloalkyl groups or $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, those recited previously herein. The term "heterocycloalkyl" as used herein, in accordance with some embodiments, also includes: bridged ring polycyclic heterocycloalkyl groups, such as but not limited to, 7-oxabicyclo[2.2.1]heptanyl; and fused ring polycyclic heterocycloalkyl groups, such as but not limited to, octahydrocyclopenta[b]pyranyl, and octahydro-1H-isochromenyl.

The term "heteroaryl," as used herein, in accordance with some embodiments, includes but is not limited to $C_5$-$C_{18}$ heteroaryl, such as but not limited to $C_5$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, those recited previously herein.

As used herein, the term "fused ring polycyclic-aryl-alkyl group" and similar terms such as, fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to indenyl, 9H-flourenyl, cyclopentanaphthenyl, and indacenyl.

The term "aralkyl," as used herein, and in accordance with some embodiments, includes but is not limited to $C_6$-$C_{24}$ aralkyl, such as but not limited to $C_6$-$C_{10}$ aralkyl, and means an aryl group substituted with an alkyl group. Examples of aralkyl groups include, but are not limited to, those recited previously herein.

The compounds according to the present invention, such as, but not limited to those represented by Formula (I), and the various groups thereof are described in further detail herein as follows.

In accordance with some embodiments, and with reference to Formula (I): Ring-A is aryl; and R$^1$ of E and R$^2$ of D are each independently selected from hydrogen, linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl.

In accordance with some embodiments, and with reference to Formula (I): m is at least 1 for at least one t; q is at least 1 for at least one s.

With further reference to Formula (I) and with some embodiments, L$^2$ is, independently for each m, and L$^5$ is, independently for each q, in each case independently selected from divalent linear or branched $C_1$-$C_{25}$ alkyl, divalent interrupted linear or branched $C_1$-$C_{25}$ alkyl, divalent linear or branched $C_1$-$C_{25}$ perhaloalkyl, and divalent interrupted linear or branched $C_1$-$C_{25}$ perhaloalkyl, where each divalent interrupted linear or branched $C_1$-$C_{25}$ alkyl and each divalent interrupted linear or branched $C_1$-$C_{25}$ perhaloalkyl are each independently interrupted with at least one interrupting group selected from the interrupting groups —O—, —C(O)O—, and —OC(O)O—.

With additional reference to Formula (I) and with some embodiments: p is at least 1 for at least one t; r is at least 1 for at least one s.

With additional reference to Formula (I) and with some embodiments, L$^3$ independently for each p, and L$^6$ independently for each r, are in each case independently represented by the following Formula (II-2),

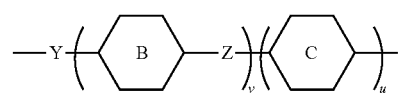

Formula (II-2)

With reference to Formula (II-2), and with some embodiments, the divalent rings,

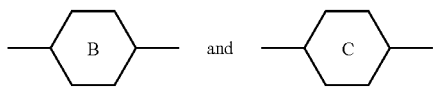

are each independently selected, for each v and each u, from phenylen-1,4-diyl, substituted phenylen-1,4-diyl, cyclohexan-1,4-diyl, substituted cyclohexan-1,4-diyl, pyrimidin-2,5-diyl, substituted pyrimidin-2,5-diyl, pyridine-2,5-diyl, substituted pyridine-2,5-diyl, naphthalene-2,6-diyl, substituted naphthalene-2,6-diyl, 1,2,3,4-tetrahydronaphthalene-2,6-diyl, 1,2,3,4-tetrahydronaphthalene-2,6-diyl in which the aromatic ring is substituted, decahydronaphthalene-2,6-diyl, indane-2,5(6)-diyl, fluorene-2,-7-diyl, phenanthrene-2,7-diyl, 9,10-dihydrophenanthrene-2,7-diyl, (1,3,4)thiadiazol-2,5-diyl, (1,3)thiazol-2,5-diyl, (1,3)thiazol-2,4-diyl, thiophen-2,4-diyl, thiophen-2,5-diyl, (1,3)dioxan-2,5-diyl, piperidin-1,4-diyl, and, piperazin-1,4-diyl.

With reference to Formula (I), and with some embodiments, $E^1$ and $E^2$ are each independently selected from hydrogen, linear or branched $C_1$-$C_{25}$ alkyl, interrupted linear or branched $C_1$-$C_{25}$ alkyl, linear or branched $C_2$-$C_{25}$ alkenyl, and interrupted linear or branched $C_2$-$C_{25}$ alkenyl, wherein each interrupted linear or branched $C_1$-$C_{25}$ alkyl and each interrupted linear or branched $C_2$-$C_{25}$ alkenyl are each independently interrupted with at least one interrupting group selected from —O—, —S—, and —C(O)O—.

With regard to $E^1$ and $E^2$ of Formula (I), there is the further proviso, with some embodiments, that $E^1$ and/or $E^2$ independently is, or is independently substituted with, at least one reactive group selected from (meth)acryloyl, unsubstituted styrene, substituted styrene, oxirane, thiirane, carboxylic acid, carboxylic acid ester, unsubstituted cyclic carboxylic acid ester, substituted cyclic carboxylic acid ester, cyclic carboxylic acid anhydride, hydroxyl, thiol, and combinations thereof.

With some embodiments, Ring-A of Formula (I) is phenyl, and the monomer represented by Formula (I) is further represented by the following Formula (I-A):

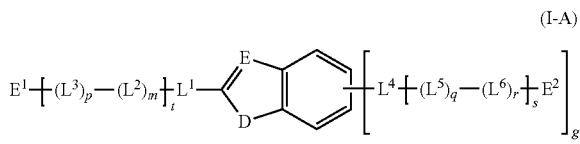

With reference to Formula (I-A), g is from 0 to 4, provided that the sum of t and g is at least 1. The groups and subscripts of Formula (I-A) are each as described previously herein with reference to Formula (I), and as described further herein.

With reference to Formula (I), and correspondingly Formula (I-A), $R^1$ of E and $R^2$ of D, with some embodiments, are each independently selected from hydrogen and linear or branched $C_1$-$C_{10}$ alkyl.

With further reference to Formula (I), and correspondingly Formula (I-A), $L^2$ is, independently for each m, and $L^5$ is, independently for each q, in each case independently selected from divalent linear or branched $C_1$-$C_{10}$ alkyl, divalent interrupted linear or branched $C_1$-$C_{10}$ alkyl, divalent linear or branched $C_1$-$C_{10}$ perfluoroalkyl, and divalent interrupted linear or branched $C_1$-$C_{10}$ perfluoroalkyl, where each divalent interrupted linear or branched $C_1$-$C_{10}$ alkyl and each divalent interrupted linear or branched $C_1$-$C_{10}$ perfluoroalkyl are each independently interrupted with at least one interrupting group selected from —O—, —C(O)O—, and —OC(O)O—.

With additional reference to Formula (I), and correspondingly Formula (I-A), independently for each $L^3$, and independently for each $L^6$, Z is, independently for each v, selected from the group consisting of a single bond, —O— and —C(O)O—.

With further additional reference to Formula (I), and correspondingly Formula (I-A), and independently for each $L^3$, and independently for each $L^6$, the divalent rings,

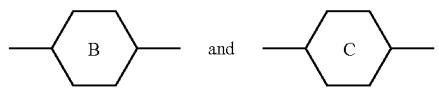

are each independently selected, for each v and each u, from phenylen-1,4-diyl, substituted phenylen-1,4-diyl, cyclohexan-1,4-diyl, and substituted cyclohexan-1,4-diyl.

With further reference to Formula (I), and correspondingly Formula (I-A), and in accordance with some embodiments, $E^1$ and $E^2$ are each independently selected from hydrogen, linear or branched $C_1$-$C_{10}$ alkyl, and interrupted linear or branched $C_1$-$C_{10}$ alkyl, where each interrupted linear or branched $C_1$-$C_{10}$ alkyl is independently interrupted with at least one interrupting group selected from —O—, —S—, and —C(O)O—.

With regard to $E^1$ and $E^2$ of Formula (I), and correspondingly Formula (I-A), there is the further proviso, with some embodiments, that at least one of $E^1$ and $E^2$ independently is, or is independently substituted with, at least one reactive group selected from the group consisting of (meth)acryloyl, unsubstituted styrene, substituted styrene, oxirane, thiirane, carboxylic acid, carboxylic acid ester, unsubstituted cyclic carboxylic acid ester, substituted cyclic carboxylic acid ester, cyclic carboxylic acid anhydride, hydroxyl, thiol, and combinations thereof.

In accordance with some embodiments and with reference to Formula (I), and correspondingly Formula (I-A), $E^1$ and $E^2$ are each independently selected from hydrogen, linear or branched $C_1$-$C_{10}$ alkyl, and interrupted linear or branched $C_1$-$C_{10}$ alkyl, where each interrupted linear or branched $C_1$-$C_{10}$ alkyl is independently interrupted with at least one interrupting group selected from —O— and —C(O)O—. With regard to $E^1$ and $E^2$ of Formula (I), and correspondingly Formula (I-A), there is the further proviso, with some embodiments, at least one of $E^1$ and $E^2$ independently is, or is independently substituted with, (meth)acryloyl.

With some embodiments of the compounds of the present invention, such as represented by Formula (I), each of $E^1$ and $E^2$ independently is, or is independently substituted with, at least one reactive group, which can be selected from those classes and examples of reactive groups recited previously herein.

With some further embodiments of the compounds of the present invention, such as represented by Formula (I): (a) $E^1$ is, or is substituted with, a reactive group selected from the group consisting of oxirane, thiirane, carboxylic acid, carboxylic acid ester, unsubstituted cyclic carboxylic acid ester, substituted cyclic carboxylic acid ester, cyclic carboxylic acid anhydride, and isocyanate; and (b) $E^2$ is, or is substituted with, a reactive group selected from the group consisting of hydroxyl, thiol, and amine.

For purposes of non-limiting illustration, and in accordance with some embodiments of the present invention, each $E^1$ and each $E^2$ are in each case independently represented by the following Formula (VII), $$(X^*)_n\text{-}(L^*)\text{-} \quad (VII)$$

With reference to Formula (VII), L* is selected from a bond, such as a single bond, multivalent hydrocarbyl, multivalent substituted hydrocarbyl, multivalent interrupted hydrocarbyl, and multivalent substituted interrupted hydrocarbyl, where each multivalent interrupted hydrocarbyl and each multivalent substituted interrupted hydrocarbyl are each independently interrupted with at least one interrupting group selected from —O—, —S—, —C(O)—, —C(O)O—, —OC(O)O—, —S(O)—, —SO$_2$—, —N(R$^9$)—, and —Si(R$^9$)(R$^{10}$)— where $R^9$ and $R^{10}$ are each independently selected from hydrogen, hydrocarbyl, and substituted hydrocarbyl, and combinations of two or more interrupting groups thereof.

With further reference to Formula (VII), subscript n in each case is independently at least 1, such as 1 to 10, or 1 to 8, or 1 to 6, or 1 to 5, or 1 to 4, or 1 to 3, or 2, or 1.

With additional reference to Formula (VII), X* in each case and independently for each n is a reactive group selected from (linear or branched $C_1$-$C_8$ alkyl)acryloyl, unsubstituted styrene, substituted styrene, oxirane, thiirane, carboxylic acid, carboxylic acid ester, unsubstituted cyclic carboxylic acid ester, substituted cyclic carboxylic acid ester, cyclic carboxylic acid anhydride, hydroxyl, thiol, amine, isocyanate, aldehyde, and combinations thereof. With further additional reference to Formula (VII), there is the proviso that for at least one of $E^1$ and $E^2$, at least one X* is selected from a reactive group.

The compounds of the present invention, such as represented by Formula (I), can be used alone or can be used to prepare other materials, such as polymers. When used to prepare polymers, the compounds of the present invention can be referred to as monomers, or monomer compounds, and polymers prepared therefrom include residues of such monomers or monomer compounds of the present invention.

In accordance with some embodiments, polymers prepared from one or more compounds of the present invention, such as represented by Formula (I), further include at least one residue of an additional monomer selected from (meth)acrylic acid, hydrocarbyl (meth)acrylate, substituted hydrocarbyl (meth)acrylate, unsubstituted styrene, substituted styrene, and combinations thereof.

With reference to Formulas (I) and (I-A), and in accordance with some further embodiments, D is O.

With reference to Formula (I), and with some embodiments of the present invention, $L^1$ and $L^4$ are each independently selected from t one of the following Formulas IIIa, IIIb, IIIc, IIId, IIIe, or IIIf:

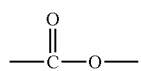

IIIa

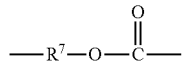

IIIb where $R^7$ is selected from hydrocarbyl and substituted hydrocarbyl,

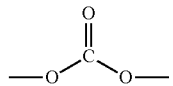

IIIc

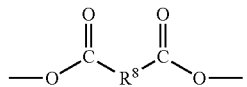

IIId where $R^8$ is selected from hydrocarbyl and substituted hydrocarbyl,

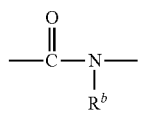

IIIe where $R^b$ is selected from hydrogen, hydrocarbyl and substituted hydrocarbyl, and

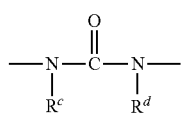

IIIf where $R^c$ and $R^d$ are each independently selected from hydrogen, hydrocarbyl and substituted hydrocarbyl.

With reference to Formulas IIIb and IIId above, $R^7$ and $R^8$ for each of $L^1$ and $L^4$ are each independently selected from divalent linear or branched $C_1$-$C_{25}$ alkyl, divalent linear or branched $C_2$-$C_{25}$ alkenyl, divalent $C_3$-$C_{12}$ cycloalkyl, divalent $C_3$-$C_{12}$ heterocycloalkyl, divalent aryl, and divalent heteroaryl.

In accordance with some embodiments, $L^1$ and $L^4$ of Formula (I) are each independently the divalent linking group represented by Formula IIId, and each $R^8$ is independently a divalent linear or branched $C_1$-$C_8$ alkyl group.

With reference to Formulas IIIe and IIIf above, and in accordance with some embodiments, $R^b$, $R^c$, and $R^d$ for each of $L^1$ and $L^4$ are each independently selected from linear or branched $C_1$-$C_{25}$ alkyl, linear or branched $C_2$-$C_{25}$ alkenyl, $C_3$-$C_{12}$ cycloalkyl, $C_3$-$C_{12}$ heterocycloalkyl, aryl, and heteroaryl.

With further reference to Formulas IIIe and IIIf above, and in accordance with some further embodiments, $R^b$, $R^c$, and $R^d$ for each of $L^1$ and $L^4$ are each independently a linear or branched $C_1$-$C_8$ alkyl group.

With some embodiments of the present invention and with reference to Formula (I) and Formula (II-1), divalent Ring-(B) and divalent Ring-(C), are each independently selected from the group consisting of divalent aryl, substituted divalent aryl, divalent heteroaryl, and substituted divalent heteroaryl.

In accordance with some further embodiments of the present invention and with reference to Formula (I) and Formula (II-2), divalent Ring-(B) and divalent Ring-(C), are each independently selected from the group consisting of phenylen-1,4-diyl, substituted phenylen-1,4-diyl, pyrimidin-2,5-diyl, substituted pyrimidin-2,5-diyl, pyridine-2,5-diyl, substituted pyridine-2,5-diyl, naphthalene-2,6-diyl, substituted naphthalene-2,6-diyl, and phenanthrene-2,7-diyl.

With some embodiments of the compounds of the present invention and with reference to Formula (I), each $L^3$ and each $L^6$, are in each case independently a divalent group selected from the following Formulas, IV(A) through IV(O):

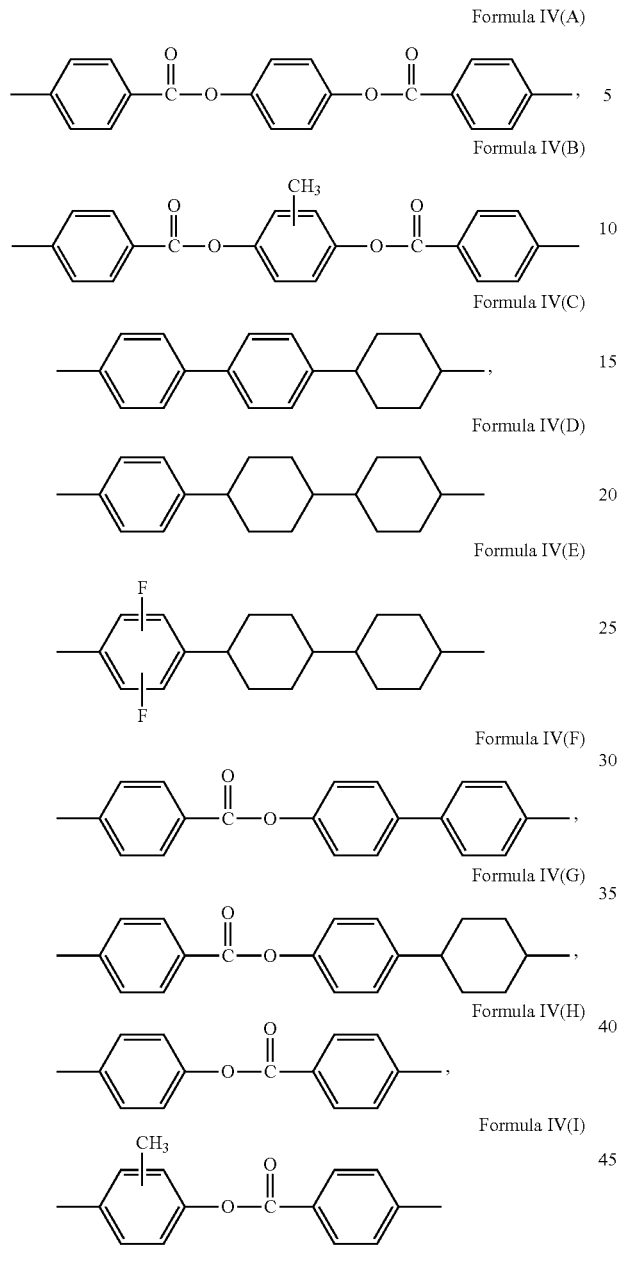

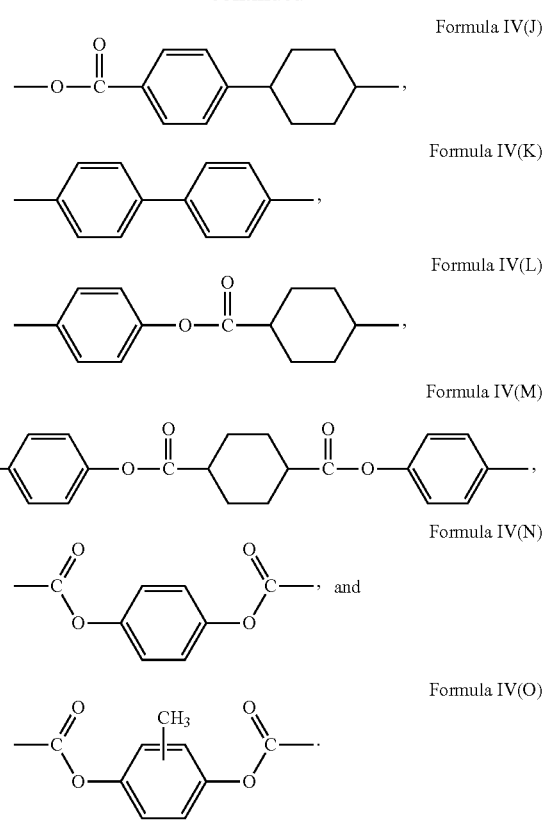

In accordance with some embodiments of the present invention and with reference to Formula (I), at least one of $L^3$ and $L^6$ independently is a mesogenic group, and the compound is a mesogenic compound. Polymers prepared from the mesogenic compounds of the present invention, such as represented by Formula (I), can have mesogenic properties, and correspondingly are mesogenic polymers. Since the polymers that include at least one residue of at least one compound represented by Formula (I), and at least one of $L^3$ and $L^6$ independently is a mesogenic group, such polymers can be described as mesogenic polymers when at least one of $L^3$ and $L^6$ independently is a mesogenic group.

Non-limiting examples of compounds according to the present invention, such as represented by Formula (I), include those represented by the following Formulas (M-1) to (M-17):

(M-1)

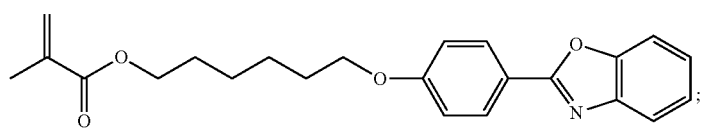

6(4-(benzo[d]oxazol-2-yl)phenoxy)hexyl methacrylate (M-2)

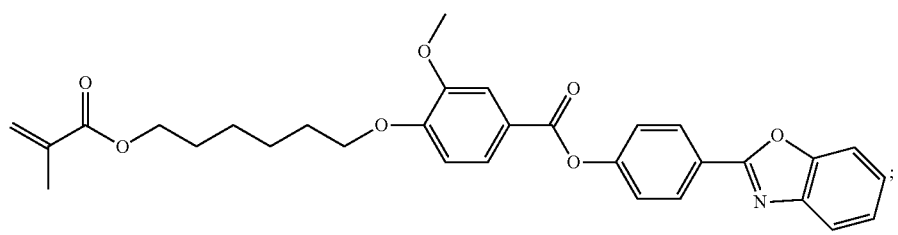

4-(benzo[d]oxazol-2-yl)phenyl 4-((6-((methacryloyloxy)hexyl)oxy)-3-methoxybenzoate -continued

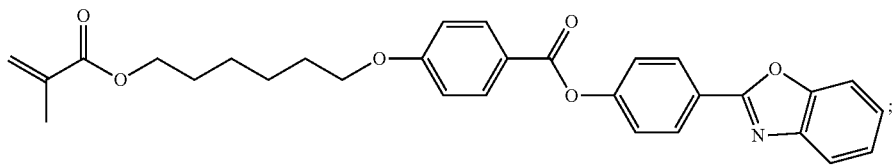

4-(benzo[d]oxazol-2-yl)phenyl 4-((6-((methacryloyloxy)hexyl)oxy)benzoate (M-3)

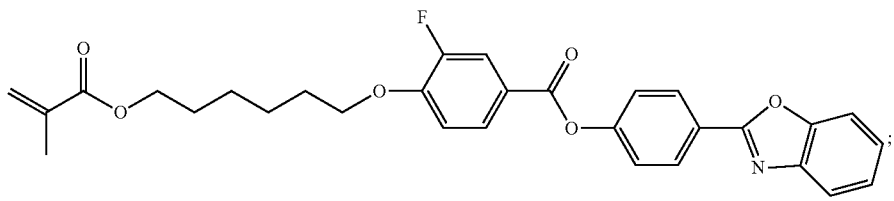

4-(benzo[d]oxazol-2-yl)phenyl 3-fluoro-4-((6-methacryloyloxy)hexyl)oxy)benzoate (M-4)

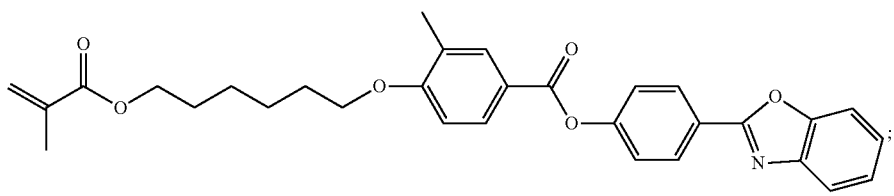

4-(benzo[d]oxazol-2-yl)phenyl 4-((6-methacryloyloxy)hexyl)oxy)-3-methylbenzoate (M-5)

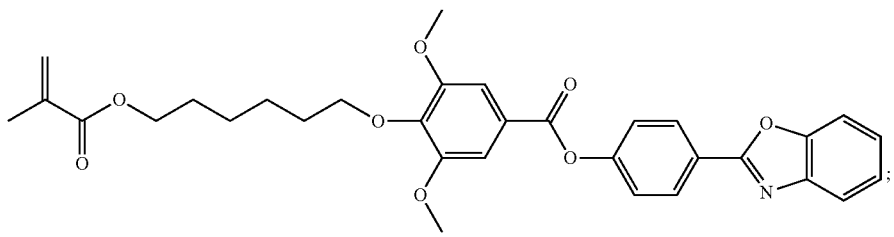

4-(benzo[d]oxazol-2-yl)phenyl 4-((6-methacryloyloxy)hexyl)oxy)-3,5-dimethylbenzoate (M-6)

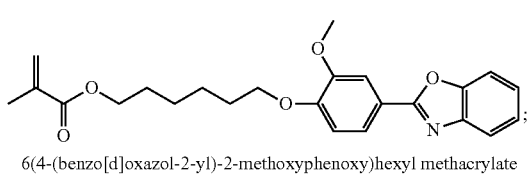

6(4-(benzo[d]oxazol-2-yl)-2-methoxyphenoxy)hexyl methacrylate (M-7)

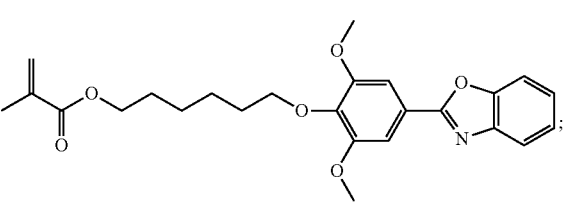

6(4-(benzo[d]oxazol-2-yl)-2,6-dimethoxyphenoxy)hexyl methacrylate (M-8)

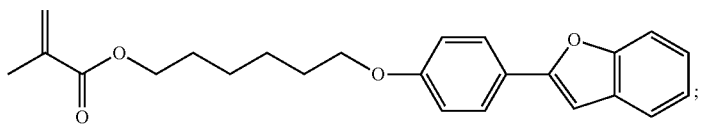

6(4-(benzofuran-2-yl)phenoxy)hexyl methacrylate (M-9)

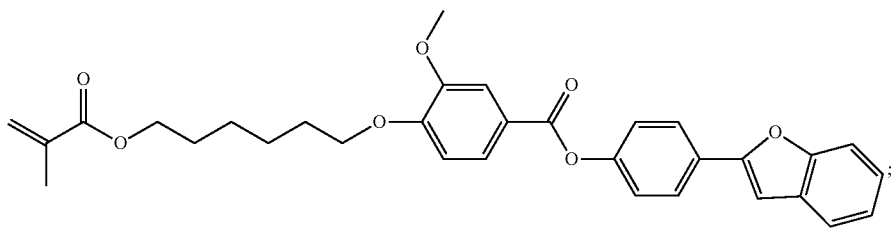

4-(benzofuran-2-yl)phenyl 4-((6-((methacryloyloxy)hexyl)oxy)-3-methoxybenzoate (M-10)

-continued

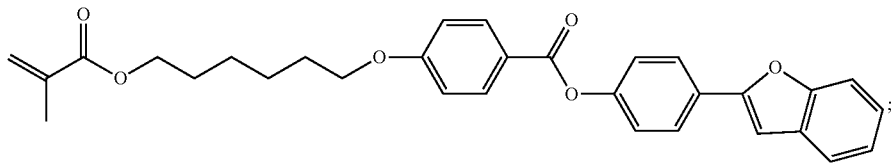

4-(benzofuran-2-yl)phenyl 4-((6-methacryloyloxy)hexyl)oxy)benzoate (M-11)

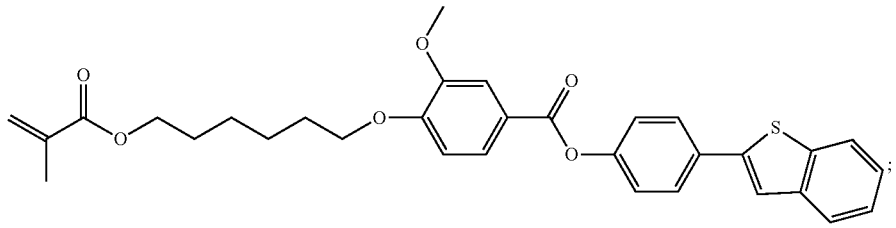

4-(benzo[b]thiophen-2-yl)phenyl 4-((6-methacryloyloxy)hexyl)oxy)-3-methylbenzoate (M-12)

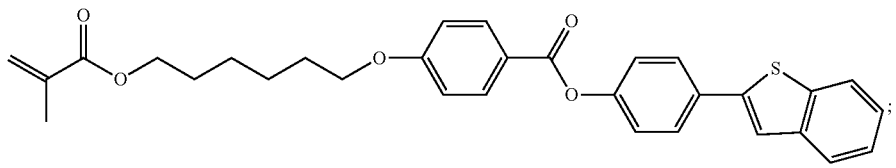

4-(benzo[b]thiophen-2-yl)phenyl 4-((6-methacryloyloxy)hexyl)oxy)benzoate (M-13)

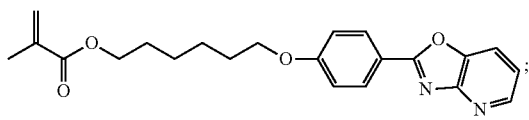

6-(4-(oxazolo[4,5-b]pyridin-2-yl)phenoxy)hexyl methacrylate (M-14)

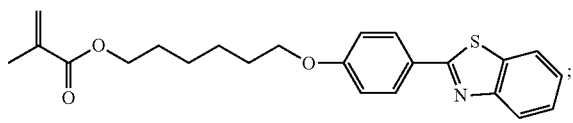

6-(4-(benzo[d]thiazol-2-yl)phenoxy)hexyl methacrylate (M-15)

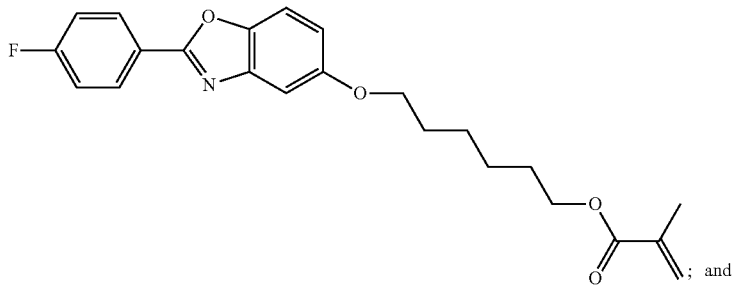

6-((2-(4-fluorophenyl)benzo[d]oxazol-5-yl)oxy)hexyl methacrylate (M-16); and

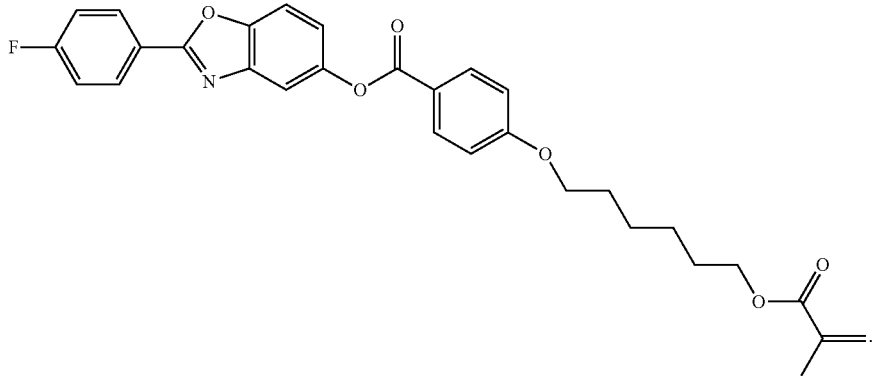

2-(4-fluorophenyl)benzo[d]oxazol-5-yl 4-((6-(methacryloyloxy)hexyl)oxy)benzoate (M-17)

Polymers prepared from the compounds of the present invention, such as represented by Formula (I), with some embodiments, further include at least one residue of at least one further monomer represented by the following Formula (V),

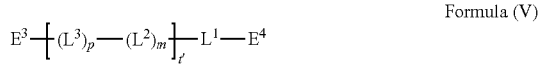

Formula (V)

With reference to Formula (V): t' is from 1 to 4; $L^1$, $L^2$, and $L^3$, are each independently as described previously herein with reference to Formula (I); m is, independently for each t', from 0 to 4; p is, independently for each t', from 0 to 4, provided that the sum of m and p is at least one for each t'.

With further reference to Formula (V), $E^3$ and $E^4$ are each independently selected from hydrogen, hydrocarbyl, interrupted hydrocarbyl, substituted hydrocarbyl, and substituted interrupted hydrocarbyl, where each interrupted hydrocarbyl and each substituted interrupted hydrocarbyl are each independently interrupted with at least one interrupting group selected from —O—, —S—, —C(O)—, —C(O)O—, —OC(O)O—, —S(O)—, —SO$_2$—, —N(R$^9$)—, and —Si(R$^9$)(R$^{10}$)— wherein $R^9$ and $R^{10}$ are each independently selected from the group consisting of hydrogen, hydrocarbyl and substituted hydrocarbyl, and combinations of two or more interrupting groups thereof.

With additional reference to Formula (V), there is the proviso that $E^3$ is, or is substituted with, at least one reactive group selected from (linear or branched $C_1$-$C_8$ alkyl)acryloyl, unsubstituted styrene, substituted styrene, oxirane, thiirane, carboxylic acid, carboxylic acid ester, unsubstituted cyclic carboxylic acid ester, substituted cyclic carboxylic acid ester, cyclic carboxylic acid anhydride, hydroxyl, thiol, amine, isocyanate, aldehyde, and combinations thereof.

With some embodiments, $E^3$ of Formula (V) is independently represented by Formula (VII) as described previously and independently herein with regard to $E^1$ and $E^2$ of Formula (I).

Polymers prepared from the compounds of the present invention, such as represented by Formula (I), with some embodiments, include at least one polymer segment represented by the following Formula (VI),

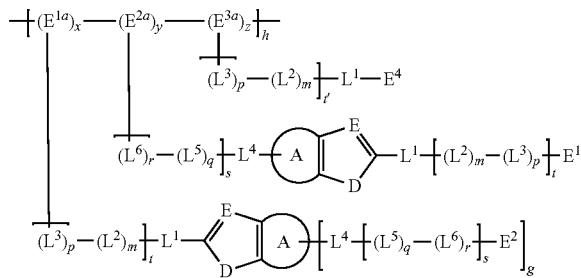

Formula (VI)

With reference to Formula (VI): $E^{1a}$ independently for each x is a divalent residue of $E^1$ of Formula (I): $E^{2a}$ independently for each y is a divalent residue of $E^2$ of Formula (I); and $E^{3a}$ independently for each z is a divalent residue of $E^3$ of Formula (V).

With further reference to Formula (VI): h is from 1 to 10,000; x is from 0 to 10 for each h; y is from 0 to 10 for each h; and z is from 0 to 10 for each h. With additional reference to Formula (VI), there is: (i) the proviso that the sum of x, y, and z is at least one for each h; and (ii) the further proviso that the sum of x and y is at least one for at least one h.

Polymers prepared from the compounds of the present invention, such as represented by Formula (I), can, with some embodiments, be selected from linear polymers, branched polymers, star polymers, graft polymers, and mixtures thereof.

Each polymer segment represented by Formula (VI) can independently have a chain architecture (or chain structure) selected from: random chain architecture (in which the monomer residues are distributed randomly along the polymer segment); block chain architecture (in which the monomer residues are distributed in blocks along the polymer segment); gradient chain architecture (in which the monomer residues are distributed in a gradient along the polymer segment); and combinations of two or more such chain architectures.

With reference to Formula (VI), and in accordance with some embodiments, $E^{1a}$, $E^{2a}$, and $E^{3a}$ are each independently a residue of a radically polymerizable group, and at least the polymer segment represented by Formula (VI) is prepared by art-recognized radical polymerization methods, such as, but not limited to, free radical polymerization methods, and living radical polymerization methods, such as atom transfer radical polymerization methods. With some embodiments of the present invention, $E^{1a}$, $E^{2a}$, and $E^{3a}$ are each independently a residue of a (meth)acryloyl group.

Polymers prepared from the compounds of the present invention, such as represented by Formula (I), include at least one polymer chain segment represented by Formula (VI) as described above. The polymer chain segment represented by Formula (VI) can represent one or more segments that form (or define) at least a portion of the chain, or backbone, architecture of the polymer. With some embodiments, the polymer chain segment represented by Formula (VI) is located in at least one of: the backbone of the polymer; one or more branches of the polymer (when the polymer is branched); and one or more arms of the polymer (when the polymer has star or comb architecture).

With some embodiments, polymers prepared from the compounds of the present invention, such as represented by Formula (I), include at least one polymer chain segment represented by Formula (VI), such as 1 to 100, or 1 to 50, or 1 to 30, or 1 to 20, or 1 to 10, or 1 to 5, or 1 to 3 polymer chain segments represented by Formula (VI).

Polymers prepared from the compounds of the present invention, such as represented by Formula (I), can have any suitable molecular weight. With some embodiments, such polymers have a Mw of from 5,000 to 2,500,000, or from 10,000 to 500,000, or from 30,000 to 200,000; and an Mn of from 1,000 to 1,000,000, or from 5,000 to 250,000, or from 20,000 to 80,000. Polymers prepared from the compounds of the present invention, such as represented by Formula (I), with some embodiments, have a polydispersity index (PDI=Mw/Mn) of at least 1.0, such as from 1.0 to 3.5, or from 1.5 to 3.5, or from 2.0 to 3.0.

The compounds of the present invention, such as represented by Formula (I), and/or polymers prepared from such compounds can be used to form or as one or more components of an alignment layer.

As used herein the term "alignment layer" means a layer that can facilitate the positioning of one or more other structures that are exposed, directly and/or indirectly, to at least a portion thereof. As used herein the term "order" means bringing into a suitable arrangement or position, such as aligning with another structure or material, or by some other force or effect. Thus, as used herein the term "order" encompasses both: (i) contact methods of ordering a material, such as by aligning with another structure or material; and (ii) non-contact methods of ordering a material, such as by exposure to an external force or effect. The term order also encompasses combinations of contact and non-contact methods.

For purposes of non-limiting illustration, liquid crystal materials, dichroic compounds, and/or photochromic-dichroic compounds that are at least partially aligned by interaction with the alignment layer, can be at least partially aligned such that the long-axis of the liquid crystal materials, dichroic compounds, and/or photochromic-dichroic compounds (such as in an activated state) are essentially parallel to at least the first general direction of the alignment layer. With some embodiments, the liquid crystal materials, dichroic compounds, and/or photochromic-dichroic compounds that are at least partially aligned by interaction with the alignment layer are bound to or reacted with the alignment layer. As used herein with reference to order or alignment of a material or structure, the term "general direction" refers to the predominant arrangement or orientation of the material, compound or structure. Further, it will be appreciated by those skilled in the art that a material, compound or structure can have a general direction even though there is some variation within the arrangement of the material, compound or structure, provided that the material, compound or structure has at least one predominate arrangement.

Alignment layers that include one or more compounds of the present invention, such as represented by Formula (I), and/or polymers prepared from such compounds, can, with some embodiments, have at least a first general direction. For example, the alignment layer can include a first ordered region having a first general direction and at least one second ordered region adjacent the first ordered region having a second general direction that is different from the first general direction. Further, the alignment layer can have a plurality of regions, each of which has a general direction that is the same or different from the remaining regions so as to form a desired pattern or design.

Alignment layers that include the compound(s) of the present invention and/or polymer(s) prepared from such compounds, can, with some embodiments, be crosslinked alignment layers, non-crosslinked alignment layers (such as, but not limited to, a thermoplastic alignment layer), and combinations thereof. With some embodiments, the alignment layer can be in the form of a film (such as formed from a thermoplastic coating composition and/or a crosslinkable coating composition), a sheet (such as formed by extrusion of a thermoplastic extrusion composition and/or a crosslinkable extrusion composition), and combinations thereof.

Alignment layers that include one or more compounds of the present invention and/or polymer(s) prepared from such compound(s), can be aligned by art-recognized methods including, but not limited to, contact methods (such as by a shear force), and non-contact methods (such as by exposure to a magnetic field, an electric field, and/or linearly polarized radiation). With some embodiments, the alignment layer is in the form of a sheet, which can be aligned by uniaxial stretching and/or during extrusion of the sheet.

Alignment layers that include one or more compounds of the present invention and/or polymer(s) prepared from such compound(s), can be used in conjunction with an optical element, which includes: an optical substrate; and in which the alignment layer resides over at least a portion of a surface of the optical substrate.

The alignment layer of the optical element, with some embodiments, is at least partially aligned by exposing at least a portion of the alignment layer to at least one of, a magnetic field, an electric field, linearly polarized radiation, and shear force, in each case in accordance with art-recognized methods.

The optical element, with some embodiments, is selected from an ophthalmic element, a display element, a window, a mirror, and a liquid crystal cell element.

The optical element, with some further embodiments, is an ophthalmic element, which is selected from a corrective lens, a non-corrective lens, a contact lens, an intra-ocular lens, a magnifying lens, a protective lens, and a visor.

The optical element, with some embodiments, includes over at least a portion of the surface of the optical substrate, at least one additional layer, where each additional layer is independently selected from a primer layer, a protective layer, an anti-reflective layer, a reflective layer, a polarizing layer, a photochromic layer, a liquid crystal layer, and combinations thereof. The primer layer, protective layer, anti-reflective layer, reflective layer, polarizing layer, photochromic layer, and liquid crystal layer, can in each case be selected from art-recognized classes and examples of each such layers.

Each optional photochromic layer of the optical element includes one or more art-recognized photochromic compounds and/or photochromic-dichroic compounds. Classes of photochromic compounds that can be included in each optional photochromic layer include, but are not limited to, indeno-fused naphthopyrans, naphtho[1,2-b]pyrans, naphtho[2,1-b]pyrans, spirofluoroeno[1,2-b]pyrans, phenanthropyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, and combinations of two or more thereof.

The photochromic compounds that can be included in the photochromic layer of the optical element include, or can be, with some embodiments, photochromic-dichroic materials and compounds. The photochromic-dichroic materials and compounds can, with some embodiments, be selected from art-recognized photochromic-dichroic materials and compounds. Photochromic-dichroic compounds typically have a photochromic group (P) and at least one lengthening agent or group (L) covalently bonded to the photochromic group. The photochromic groups of the photochromic-dichroic compounds can be selected from those classes and examples as described previously herein with regard to the photochromic compounds, such as, but not limited to, pyrans, oxazines, fulgides, and indeno-fused naphthopyrans. Examples of photochromic-dichroic compounds that can be included in the photochromic layer of the optical elements, include, but are not limited to those disclosed in U.S. Pat. No. 7,256,921 B2 at column 19, line 3 through column 22, line 46, which disclosure is incorporated herein by reference. Examples of lengthening groups (L) and photochromic groups (P) include, but are not limited to those disclosed in U.S. Pat. No. 7,256,921 B2 at column 22, line 47 through column 35, line 27, which disclosure is incorporated herein by reference.

The photochromic compounds and/or photochromic-dichroic compounds can be present in the photochromic layer, in amounts (or ratios) such that the resulting photochromic layer (and the coated optical element) exhibits desired optical properties. For purposes of non-limiting illustration, the amount and types of photochromic compounds and/or photochromic-dichroic compounds can be selected such that the photochromic layer is clear or colorless when the photochromic compounds and/or photochromic-dichroic compounds are in the closed-form (e.g., in the bleached or unactivated state), and can exhibit a desired resultant color when the photochromic compounds and/or photochromic-dichroic compounds are in the open-form (e.g., when activated by actinic radiation). The precise amount of the photochromic compounds and/or photochromic-dichroic compounds that are utilized is not critical, provided that at least a sufficient amount is used to produce the desired effect. The particular amount of the photochromic compounds and/or photochromic-dichroic compounds used can depend on a variety of factors, such as but not limited to, the absorption characteristics of the photochromic compounds and/or photochromic-dichroic compounds, and the color and intensity of the color desired upon activation. In accordance with some embodiments of the method of the present invention, the amount of the photochromic compound(s) and/or photochromic-dichroic compound(s) that are present in the photochromic layer formed over the optical substrate of the optical element can range from 0.01 to 40 weight percent, or from 0.05 to 15, or from 0.1 to 5 weight percent, based on the weight of the photochromic coating layer.

With some embodiments, two or more photochromic compounds are used in combination with each other and/or with one or more photochromic-dichroic compounds, so as to complement one another and to produce a desired color or hue. For example, mixtures of photochromic compounds can be used with some embodiments to attain certain activated colors, such as a near neutral gray or near neutral brown. See, for example, U.S. Pat. No. 5,645,767, column 12, line 66 to column 13, line 19, the disclosure of which is specifically incorporated by reference herein, which describes the parameters that define neutral gray and brown colors.

The photochromic layer can have any suitable thickness, provided it provides a desirable level of photochromic properties, such as but not limited to a desirable range of optical density values. With some embodiments, each photochromic layer independently has a thickness of from 0.5 to 50 microns, such as from 1 to 45 microns, or from 2 to 40 microns, or from 5 to 30 microns, or from 10 to 25 microns.

The present invention is more particularly described in the following examples, which are intended as illustrative only, since numerous modifications and variations therein will be apparent to those skilled in the art.

EXAMPLES

Compounds according to the present invention can be prepared in accordance with the synthetic procedures described in the following Examples 1 through 17.

Example 1

Step 1

While stirring under a nitrogen atmosphere, 4-hydroxybenzoic acid (20.8 g) and 2-aminophenol (16.4 g) were added to dichlorobenzene (150 mL) in a single neck round bottom flask fitted with a Dean-Stark trap and reflux condenser. Boric acid (1.2 g) was added and the reaction mixture was refluxed at 205° C. for 22 hours. After cooling to room temperature, the solidified mixture was added to hexanes (600 mL) and stirred for 30 minutes. The precipitated solid was collected and dried under vacuum to yield an off-white powder (29.13 g). NMR spectrum of the resulting material was consistent with 4-benzo[d]oxazol-2-yl)phenol.

Step 2

While stirring under a nitrogen atmosphere, the product from Step 1 (10.0 g), 6-chlorohexan-1-ol (7.11 g) and potassium carbonate (9.81 g) were combined in dimethylformamide (70 mL). The reaction mixture was heated to 80° C. for 18 hours. After cooling to room temperature, the reaction mixture was poured into ice water. The precipitated solid was collected and dried under vacuum to yield an off-white powder (14.72 g). NMR spectrum of the resulting material was consistent with 6-(4-(benzo[d]oxazol-2-yl)phenoxy)hexan-1-ol.

Step 3

While stirring under a nitrogen atmosphere, the product from Step 2 (7.00 g), triethylamine (5.70 g), dimethylaminopyridine (0.035 g) and 3,5-di-tert-4-butylhydroxytoluene (0.10 g) were dissolved in dichloromethane (100 mL). The reaction mixture was cooled in an ice bath and methacryloyl chloride (3.53 g) was added slowly. After addition was complete, the reaction mixture was allowed to warm to room temperature and stirred for 16 hours. The reaction mixture was washed with saturated sodium bicarbonate and brine, followed by drying with magnesium sulfate. After removing organic solvent under reduced pressure, the crude residue was purified by silica gel chromatography and recrystallization from hexanes/ethyl acetate to yield a colorless solid (5.04 g). NMR spectrum of the resulting material was consistent with 6(4-(benzo[d]oxazol-2-yl)phenoxy)hexyl methacrylate.

Example 2

While stirring under a nitrogen atmosphere, the product from Example 1, Step 1 (0.69 g), 4-((6-(methacryloyloxy)hexyl)oxy)-3-methoxybenzoic acid (1.20 g), dimethylaminopyridine (0.04 g), 3,5-di-tert-4-butylhydroxytoluene (0.10 g) and N,N'-dicyclohexylcarbodiimide (0.74 g) were dissolved in dichloromethane (20 ml). After 16 hours, the reaction mixture was filtered to remove urea byproduct and the filtrate was concentrated under reduced pressure. The residue was purified by silica gel chromatography followed by recrystallization from hexanes/ethyl acetate to yield a colorless solid (1.44 g). NMR spectrum of the resulting material was consistent with 4-(benzo[d]oxazol-2-yl)phenyl 4-((6-((methacryloyloxy)hexyl)oxy)-3-methoxybenzoate.

Example 3

The procedure of Example 2 was followed, except an equimolar amount of 4-((6-(methacryloyloxy)hexyl)oxy)benzoic acid was used in place of 4-((6-(methacryloyloxy)hexyl)oxy)-3-methoxybenzoic acid. A colorless solid (4.05 g) was obtained and NMR spectrum was consistent with 4-(benzo[d]oxazol-2-yl)phenyl 4-((6-methacryloyloxy)hexyl)oxy)benzoate.

Example 4

The procedure of Example 2 was followed, except an equimolar amount of 3-fluoro-4-((6-(methacryloyloxy)hexyl)oxy)benzoic acid was used in place of 4-((6-(methacryloyloxy)hexyl)oxy)-3-methoxybenzoic acid. A colorless solid (2.49 g) was obtained and NMR spectrum was consistent with 4-(benzo[d]oxazol-2-yl)phenyl 3-fluoro-4-((6-methacryloyloxy) hexyl)oxy)benzoate.

Example 5

The procedure of Example 2 was followed, except an equimolar amount of 4-((6-(methacryloyloxy)hexyl)oxy)-3-methylbenzoic acid was used in place of 4-((6-(methacryloyloxy)hexyl)oxy)-3-methoxybenzoic acid. A colorless solid (0.61 g) was obtained and NMR spectrum was consistent with 4-(benzo[d]oxazol-2-yl)phenyl 4-((6-methacryloyloxy)hexyl)oxy)-3-methylbenzoate.

Example 6

Step 1

Syringic acid (18.7 g) was added to a solution of potassium hydroxide (13.24 g) in ethanol (225 mL)/water (75 mL) and heated to reflux for 1 hour. After cooling to room temperature, 2-((6-chlorohexyl)oxy)tetrahydro-2H-pyran (25.0 g) and potassium iodide (0.5 g) in ethanol/water mixture (75 mL) were added drop wise and the reaction was refluxed for 72 hours. Ethanol was removed under reduced pressure and the aqueous mixture was neutralized with 1.0 M hydrochloric acid then extracted with dichloromethane. The organic layers were combined, dried with magnesium sulfate and concentrated under reduced pressure. The residue (37.4 g) was used without further purification.

Step 2

While stirring under a nitrogen atmosphere, the product from Step 1 (9.94 g), the product from Example 1, Step 1 (5.00 g), dimethylaminopyridine (0.03 g) and N,N'-dicyclohexylcarbodiimide (5.36 g) were dissolved in dichloromethane (120 ml). After 24 hours, the reaction mixture was filtered to remove urea byproduct and the filtrate was concentrated under reduced pressure. The crude residue was purified by silica gel chromatography to yield a colorless solid (4.56 g).

Step 3

The product from Step 2 (4.50 g) was dissolved in tetrahydrofuran (40 mL) with methanol (40 mL). p-Toluenesulfonic acid monohydrate (0.15 g) was added and the mixture was heated to reflux. After 6 hours, the mixture was cooled to room temperature, the volume was decreased under reduced pressure and the concentrate was added to water to precipitate the product. A colorless solid was collected (3.78 g).

Step 4

The procedure of Example 1, Step 3 was followed, substituting the product of Step 3 above (3.70 g) in place of the product of Example 1, Step 2. A colorless solid (2.60 g) was obtained and NMR spectrum was consistent with 4-(benzo[d]oxazol-2-yl)phenyl 4-((6-methacryloyloxy)hexyl)oxy)-3,5-dimethylbenzoate.

Example 7

Step 1

Vanillic acid (8.41 g) and 2-aminophenol (5.46 g) were combined in a 100 mL round bottom flask. Trimethylsilyl polyphosphate (25 mL) was added neat and the mixture was heated to 180° C. for 45 minutes. The black mixture was poured over ice and stirred for 16 hours. The precipitate was filtered and dried to yield a greenish grey powder (10.63 g). NMR spectrum was consistent with 4-(benzo[d]oxazol-2-yl)-2methoxyphenol.

Steps 2 and 3

The procedure of Example 1, Steps 2 and 3 were followed, except an equimolar amount of the product of Step 1 above was used in place of the product of Example 1, Step 2 to yield an off-white solid (2.60 g) intermediate after Step 2. The final product was a colorless solid (1.02 g) with an NMR spectrum consistent with 6-(4-(benzo[d]oxazol-2-yl)-2-methoxyphenoxy)hexyl methacrylate.

Example 8

Step 1

The procedure of Example 7, Step 1 was followed, except an equimolar amount of syringic acid was used in place of vanillic acid. A purple powder (10.84 g) was obtained and NMR spectrum was consistent with 4-(benzo[d]oxazol-2-yl)-2,6-dimethoxyphenol.

Steps 2 and 3

The procedure of Example 1, Steps 2 and 3 were followed, except an equimolar amount of the product of Step 1 above was used in place of the product of Example 1, Step 2 to yield a red oil (2.95 g) after Step 2. The final product after Step 3 was an off-white solid (1.79 g) with an NMR spectrum consistent with 6-(4-(benzo[d]oxazol-2-yl)-2,6-dimethoxyphenoxy)hexyl methacrylate.

Example 9

Step 1

Benzo[b]furan-2-ylboronic acid (9.0 g), 4-iodophenol (11.12 g), and sodium carbonate (10.71 g) were added to a mixture of acetone (270 mL) and water (315 mL). The mixture was de-gassed for 15 minutes, palladium acetate (1.13 g) was added and the reaction stirred at room temperature for 5 hours. Acetone was removed under reduced pressure and the aqueous layer was extracted with ethyl acetate. The organic extracts were combined, dried with magnesium sulfate, filtered over celite and concentrated under reduced pressure. The residue was purified by silica gel chromatography followed by recrystallization from hexanes/ethyl acetate to yield colorless crystals (8.58 g).

Steps 2 and 3

The procedure of Example 1, Steps 2 and 3 were followed, except an equimolar amount of the product of Step 1 above (2.343 g) was used in place of the product of Example 1, Step 2 to yield a colorless solid (3.23 g) after Step 2. The final product after Step 3 was a colorless solid (2.45 g) with an NMR spectrum consistent with 6-(4-(benzofuran-2-yl)phenoxy)hexyl methacrylate.

Example 10

While stirring under a nitrogen atmosphere, the product from Example 9, Step 1 (2.50 g), 4-((6-(methacryloyloxy)hexyl)oxy)-3-methoxybenzoic acid (4.40 g), dimethylaminopyridine (0.15 g), 3,5-di-tert-4-butylhydroxytoluene (0.10 g) and N,N'-dicyclohexylcarbodiimide (2.70 g) were dissolved in dichloromethane (60 ml). After 16 hours, the reaction mixture was filtered to remove urea byproduct and the filtrate was concentrated under reduced pressure. The crude residue was purified by silica gel chromatography followed by recrystallization from hexanes/dichloromethane to yield a colorless solid (4.68 g). NMR spectrum of the resulting material was consistent with 4-(benzofuran-2-yl)phenyl 4-((6-((methacryloyloxy)hexyl)oxy)-3-methoxybenzoate.

Example 11

The procedure of Example 10 was followed, except an equimolar amount of 4-((6-(methacryloyloxy)hexyl)oxy) benzoic acid was used in place of 4-((6-(methacryloyloxy) hexyl)oxy)-3-methoxybenzoic acid. A colorless solid (4.03 g) was obtained with an NMR spectrum consistent with 4-(benzofuran-2-yl)phenyl 4-((6-methacryloyloxy)hexyl) oxy)benzoate.

Example 12

Step 1

The procedure of Example 9, Step 1 was followed, except an equimolar amount of benzo[b]thiophen-2-ylboronic acid was used in place of benzo[b]furan-2-ylboronic acid to yield a colorless solid (8.63 g).

Step 2

The procedure of Example 10 was followed, except an equimolar amount of the product of Step 1 was used in place of the product of Example 9, Step 1. A colorless solid (3.96 g) was obtained and NMR spectrum was consistent with 4-(benzo[b]thiophen-2-yl)phenyl 4-((6-(methacryloyloxy) hexyl)oxy)-3-methoxybenzoate.

Example 13

While stirring under a nitrogen atmosphere, the product from Example 12, Step 1 (2.50 g), 4-((6-(methacryloyloxy) hexyl)oxy)benzoic acid (3.71 g), dimethylaminopyridine (0.13 g), 3,5-di-tert-4-butylhydroxytoluene (0.10 g) and N,N'-dicyclohexylcarbodiimide (2.50 g) were dissolved in dichloromethane (60 ml). After 16 hours, the reaction mixture was filtered to remove urea byproduct and the filtrate was concentrated under reduced pressure. The crude residue was purified by silica gel chromatography followed by recrystallization from hexanes/dichloromethane to yield a colorless solid (3.84 g). NMR spectrum of the resulting material was consistent with 4-(benzo[b]thiophen-2-yl)phenyl 4-((6-((methacryloyloxy) hexyl)oxy)benzoate.

Example 14

Step 1

4-(Trifluoromethyl)phenol (10.0 g) and 2-amino-3-hydroxypyridine (8.15 g) were combined in 1.0 N sodium hydroxide (245 mL) and heated to 80° C. After 2 hours, the reaction mixture was neutralized with 1.0 M hydrochloric acid and precipitate was collected. Recrystallization with methanol and water yielded a light brown solid (9.80 g).

Steps 2 and 3

The procedure of Example 1, Steps 2 and 3 were followed, except the product of Step 1 above (3.00 g) was used in place of the product of Example 1, Step 2 to yield an off-white solid (3.67 g). The final product after Step 3 was a colorless solid (2.15 g) with an NMR spectrum consistent with 6-(4-(oxazolo[4,5-b]pyridin-2-yl)phenoxy)hexyl methacrylate.

Example 15

Step 1

While stirring under a nitrogen atmosphere, 2-(4-methoxyphenyl)benzo[d]thiazole (5.0 g) was dissolved in dichloromethane (50 mL) and cooled in an ice bath. Boron tribromide (10.38 g) was added slowly and the reaction mixture was allowed to warm to room temperature. After 16 hours, the reaction was quenched with water and 1.0 M hydrochloric acid. The layers were separated and the organic layer was washed with 1.0 M hydrochloric acid followed by brine. The organic layer was dried with magnesium sulfate, concentrated under reduced pressure and the product was precipitated from tetrahydrofuran with hexanes to yield a colorless solid (4.60 g).

Steps 2 and 3

The procedure of Example 1, Steps 2 and 3 were followed, except the product of Step 1 above (3.00 g) was used in place of the product of Example 1, Step 2 to yield an off-white solid (2.96 g). The final product after Step 3 was a colorless solid (1.26 g) with an NMR spectrum consistent with 6-(4-(benzo[d]thiazol-2-yl)phenoxy)hexyl methacrylate.

Example 16

Step 1

While stirring under a nitrogen atmosphere, 2-amino-4-methoxyphenol (3.0 g) and 4-fluorobenzaldehyde (4.1 g) were combined in methanol (40 mL) and heated at 45° C. for 16 hours. Methanol was removed under vacuum to give the Schiff base as an orange solid. After dissolving in dichloromethane (50 mL), 2,3-Dichloro-5,6-dicyano-1,4-benzoquinone (DDQ, 6.0 g) was added portion wise and the reaction mixture became a dark purple color as the solution stirred for 30 minutes. Dichloromethane was removed under vacuum and the residue was taken up in ethyl acetate, washed with saturated sodium bicarbonate followed by brine and dried with sodium sulfate. The material was purified by silica gel chromatography to yield a colorless solid (4.64 g).

Step 2

The procedure of Example 15, Step 1 was followed, except the product of Step 1 above (4.5 g) was used in place of the commercially available material to yield a colorless solid (3.82 g) with an NMR spectrum consistent with 2-(4-fluorophenyl)benzo[d]oxazol-5-ol.

Steps 3 and 4

The procedure of Example 1, Steps 2 and 3 were followed, except the product of Step 2 above (2.80 g) was used in place of the product of Example 1, Step 2 to yield an off-white solid (3.78 g). The final product after Step 4 was a colorless solid (3.02 g) with an NMR spectrum consistent with 6-((2-(4-fluorophenyl)benzo[d]oxazol-5-yl)oxy)hexyl methacrylate.

Example 17

The procedure of Example 13 was followed, except the product of Example 16, Step 2 (1.0 g) was used in place of the product of Example 12, Step 1. A colorless solid (1.37 g) was obtained having an NMR spectrum that was consistent with 2-(4-fluorophenyl)benzo[d]oxazol-5-yl 4-((6-(methacryloyloxy)hexyl)oxy)benzoate.

The present invention has been described with reference to specific details of particular embodiments thereof. It is not intended that such details be regarded as limitations upon the scope of the invention except insofar as to the extent that they are included in the accompanying claims.

What is claimed is:

1. A compound represented by the following Formula (I):

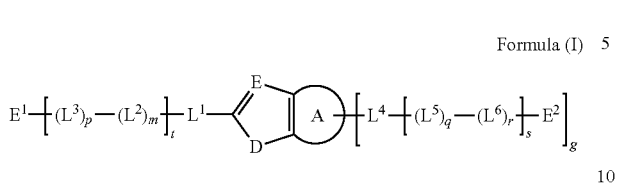

Formula (I)

wherein,
Ring-A is phenyl,
E is N or C—$R^1$,
D is selected from the group consisting of O, S, and N—$R^2$,
wherein $R^1$ of E and $R^2$ of D are each independently selected from the group consisting of hydrogen, linear or branched $C_1$-$C_{10}$ alkyl, linear or branched $C_2$-$C_{10}$ alkenyl, $C_3$-$C_{10}$ cycloalkyl, and phenyl,
$L^1$ and $L^4$ are each independently selected from at least one of:
a single bond; —O—; —S—; —C(O)—; —S(O)—; —$SO_2$—; —N=N—; and —N($R_{11}'$)— where $R_{11}'$ is selected from the group consisting of hydrogen, linear or branched $C_1$-$C_{10}$ alkyl, $C_3$-$C_{10}$ cycloalkyl, and phenyl;
t is 0 to 4,
s is, independently for each g, from 1 to 4,
g is 0 to 6, provided that the sum of t and g is at least 1,
m is, independently for each t, from 0 to 4, provided that m is at least 1 for at least one t,
q is, independently for each s, from 0 to 4, provided that q is at least 1 for at least one s,
$L^2$ independently for each m, and $L^5$ independently for each q, are in each case independently selected from the group consisting of divalent linear or branched $C_1$-$C_{10}$ alkyl, divalent interrupted linear or branched $C_1$-$C_{10}$ alkyl, wherein each divalent interrupted linear or branched $C_1$-$C_{10}$ alkyl is independently interrupted with at least one interrupting group selected from the group consisting of —O—, —C(O)O—, and —OC(O)O—,
p is, independently for each t, from 1 to 4,
r is, independently for each s, from 1 to 4,
$L^3$ independently for each p, and $L^6$ independently for each r, are in each case independently represented by the following Formula (II-2),

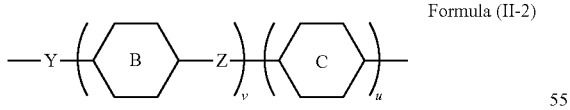

Formula (II-2)

Y is, independently for each p and independently for each r, a divalent linking group selected from the group consisting of a single bond, —O—, —S—, —C(O)—, —C(O)O—, and —OC(O)O—,
v and u are each independently, for each p and each r, 0 to 5, provided that the sum of v and u is at least 2,
Z is, independently for each v, a divalent linking group selected from the group consisting of a single bond, —O—, —S—, —C(O)—, —C(O)O—, and —OC(O)O—, wherein the divalent rings,

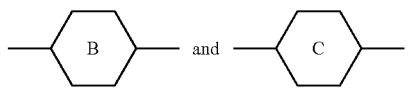

are each independently selected, for each v and each u, from the group consisting of phenylen-1,4-diyl, cyclohexan-1,4-diyl, pyrimidin-2,5-diyl, pyridine-2,5-diyl, naphthalene-2,6-diyl, 1,2,3,4-tetrahydronaphthalene-2,6-diyl, decahydronaphthalene-2,6-diyl, indane-2,5(6)-diyl, fluorene-2,-7-diyl, phenanthrene-2,7-diyl, 9,10-dihydrophenanthrene-2,7-diyl, (1,3,4)thiadiazol-2,5-diyl, (1,3)thiazol-2,5-diyl, (1,3)thiazol-2,4-diyl, thiophen-2,4-diyl, thiophen-2,5-diyl, (1,3)dioxan-2,5-diyl, piperidin-1,4-diyl, and, piperazin-1,4-diyl, and $E^1$ and $E^2$ are each independently selected from the group consisting of linear or branched $C_1$-$C_{10}$ alkyl, and interrupted linear or branched $C_1$-$C_{10}$ alkyl, wherein each interrupted linear or branched $C_1$-$C_{10}$ alkyl is independently interrupted with at least one interrupting group selected from the group consisting of —O— and —C(O)O—, provided that each of $E^1$ and $E^2$ independently is, or is independently substituted with, at least one reactive group selected from the group consisting of (linear or branched $C_1$-$C_8$ alkyl)acryloyl, unsubstituted styrene, substituted styrene, oxirane, thiirane, unsubstituted cyclic carboxylic acid ester, substituted cyclic carboxylic acid ester, cyclic carboxylic acid anhydride, thiol, amine, isocyanate, and combinations thereof, provided that a direct $L^1$-$L^2$ link between $L^1$ and $L^2$ is free of two heteroatoms linked together, a direct $L^1$-$L^3$ link between $L^1$ and $L^3$ is free of two heteroatoms linked together, and each direct $L^2$-$L^3$ link between each directly linked $L^2$ and $L^3$ is free of two heteroatoms linked together, and further provided that a direct $L^4$-$L^5$ link between $L^4$ and $L^5$ is free of two heteroatoms linked together, a direct $L^4$-$L^6$ link between $L^4$ and $L^6$ is free of two heteroatoms linked together, and each direct $L^5$-$L^6$ link between each directly linked $L^5$ and $L^6$ is free of two heteroatoms linked together, and wherein at least one of $L^3$ and $L^6$ independently is a mesogenic group, and said compound is a mesogenic compound.

2. The compound of claim 1 wherein,
each of $E^1$ and $E^2$ independently is, or is independently substituted with, at least one reactive group selected from the group consisting of (meth)acryloyl, unsubstituted styrene, substituted styrene, oxirane, thiirane, unsubstituted cyclic carboxylic acid ester, substituted cyclic carboxylic acid ester, cyclic carboxylic acid anhydride, thiol, and combinations thereof.

3. The compound of claim 2 wherein,
$R^1$ of E and $R^2$ of D are each independently selected from the group consisting of hydrogen and linear or branched $C_1$-$C_{10}$ alkyl,
independently for each $L^3$, and independently for each $L^6$,
Z is, independently for each v, selected from the group consisting of a single bond, —O— and —C(O)O—, and the divalent rings,

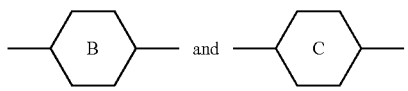

are each independently selected, for each v and each u, from the group consisting of phenylen-1,4-diyl, and cyclohexan-1,4-diyl, substituted cyclohexan 1,4 diyl, and $E^1$ and $E^2$ are each independently selected from the group consisting of linear or branched $C_1$-$C_{10}$ alkyl, and interrupted linear or branched $C_1$-$C_{10}$ alkyl, wherein each interrupted linear or branched $C_1$-$C_{10}$ alkyl is independently interrupted with at least one interrupting group selected from the group consisting of —O— and —C(O)O—, provided that each of $E^1$ and $E^2$ independently is, or is substituted with, at least one reactive group selected from the group consisting of (meth)acryloyl, unsubstituted styrene, substituted styrene, oxirane, thiirane, unsubstituted cyclic carboxylic acid ester, substituted cyclic carboxylic acid ester, cyclic carboxylic acid anhydride, thiol, and combinations thereof.

4. The compound of claim 3 wherein,
$E^1$ and $E^2$ are each independently selected from the group consisting of linear or branched $C_1$-$C_{10}$ alkyl, and interrupted linear or branched $C_1$-$C_{10}$ alkyl, wherein each interrupted linear or branched $C_1$-$C_{10}$ alkyl is independently interrupted with at least one interrupting group selected from the group consisting of —O— and —C(O)O—, provided that each of $E^1$ and $E^2$ independently is, or is independently substituted with, (meth)acryloyl.

5. The compound of claim 3, wherein D is O.

6. The compound of claim 1, wherein $L^1$ and $L^4$ are each independently selected from the group consisting of one of the following Formulas IIIa, IIIc, IIIe, or IIIf,

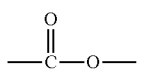

IIIa

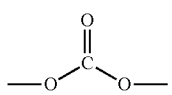

IIIc

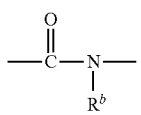

IIIe wherein $R^b$ is selected from the group consisting of hydrogen, linear or branched $C_1$-$C_{10}$ alkyl, $C_3$-$C_{10}$ cycloalkyl, and phenyl, and

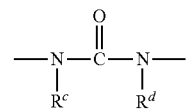

IIIf wherein $R^c$ and $R^d$ are each independently selected from the group consisting of hydrogen, linear or branched $C_1$-$C_{10}$ alkyl, $C_3$-$C_{10}$ cycloalkyl, and phenyl.

7. The compound of claim 2, wherein at least one of, divalent Ring-(B) and divalent Ring-(C), are each independently selected from the group consisting of phenylen-1,4-diyl, pyrimidin-2,5-diyl, pyridine-2,5-diyl, naphthalene-2,6-diyl, and phenanthrene-2,7-diyl.

8. The compound of claim 3, wherein each $L^3$ and each $L^6$, are in each case independently selected from the group consisting of the following formulas,

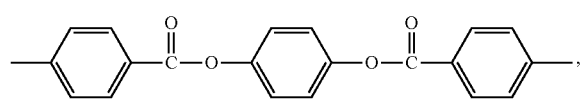

Formula IV(A)

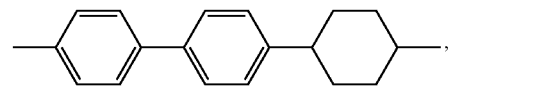

Formula IV(C)

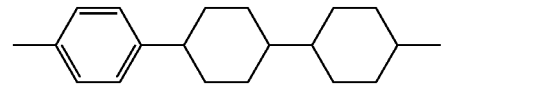

Formula IV(D)

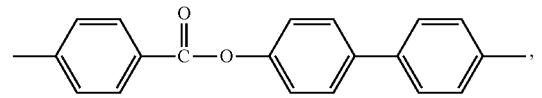

Formula IV(F)

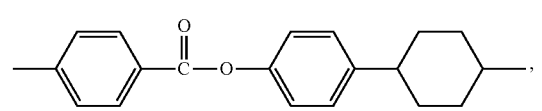

Formula IV(G)

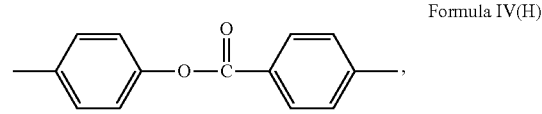

Formula IV(H)

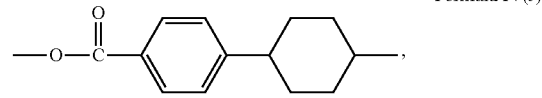

Formula IV(J)

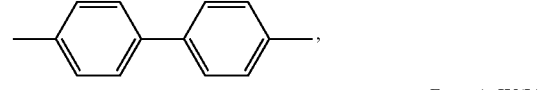

Formula IV(K)

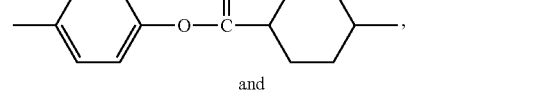

Formula IV(L)

and

Formula IV(M)

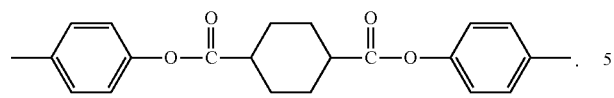

9. The compound of claim 1 wherein,
E$^1$ is, or is substituted with, a reactive group selected from the group consisting of oxirane, thiirane, unsubstituted cyclic carboxylic acid ester, substituted cyclic carboxylic acid ester, cyclic carboxylic acid anhydride, and isocyanate, and
E$^2$ is, or is substituted with, a reactive group selected from the group consisting of thiol, and amine.

* * * * *

UNITED STATES PATENT AND TRADEMARK OFFICE
CERTIFICATE OF CORRECTION

PATENT NO. : 10,875,833 B2
APPLICATION NO. : 15/573212
DATED : December 29, 2020
INVENTOR(S) : Anil Kumar et al.

Page 1 of 1

It is certified that error appears in the above-identified patent and that said Letters Patent is hereby corrected as shown below:

In the Claims

Column 33, Lines 11-12, Claim 3, after "diyl," delete "substituted cyclohexan 1,4 diyl,"

Signed and Sealed this
Fifth Day of October, 2021

Drew Hirshfeld
*Performing the Functions and Duties of the*
*Under Secretary of Commerce for Intellectual Property and*
*Director of the United States Patent and Trademark Office*